US012011274B2

(12) United States Patent
Clarkson et al.

(10) Patent No.: US 12,011,274 B2
(45) Date of Patent: Jun. 18, 2024

(54) MULTI-LEAD MEASUREMENT OF BIOPOTENTIALS WITH WEARABLE DEVICE

(71) Applicant: Verily Life Sciences LLC, South San Francisco, CA (US)

(72) Inventors: Jeffrey P. Clarkson, Burlingame, CA (US); Junjia Ding, San Mateo, CA (US); David Da He, San Mateo, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 296 days.

(21) Appl. No.: 17/393,700

(22) Filed: Aug. 4, 2021

(65) Prior Publication Data

US 2022/0039723 A1   Feb. 10, 2022

Related U.S. Application Data

(60) Provisional application No. 63/063,005, filed on Aug. 7, 2020.

(51) Int. Cl.
*A61B 5/308* (2021.01)
*A61B 5/00* (2006.01)
(Continued)

(52) U.S. Cl.
CPC .............. *A61B 5/308* (2021.01); *A61B 5/256* (2021.01); *A61B 5/271* (2021.01); *A61B 5/28* (2021.01);
(Continued)

(58) Field of Classification Search
None
See application file for complete search history.

(56) References Cited

U.S. PATENT DOCUMENTS 6,871,089 B2   3/2005  Korzinov et al.
7,502,643 B2   3/2009  Farringdon et al.
(Continued)

FOREIGN PATENT DOCUMENTS

EP        1519677 B9     3/2010
WO   2014189982 A2    11/2014
WO   2018231444 A2    10/2018

OTHER PUBLICATIONS

International Search Report and Written Opinion, mailed Nov. 5, 2021, in corresponding International Patent Application No. PCT/US2021/044519, 12 pages.
(Continued)

*Primary Examiner* — Kennedy Schaetzle
(74) *Attorney, Agent, or Firm* — CHRISTENSEN O'CONNOR JOHNSON KINDNESS PLLC (57) ABSTRACT

A biopotential measurement device including a plurality of sensing electrodes and a controller is described. The plurality of sensing electrodes is adapted to measure one or more biopotential signals when the plurality of sensing electrodes is worn. The controller is coupled to the plurality of sensing electrodes and memory that stores instructions that when executed by the controller cause the biopotential measurement device to perform operations. The operations include collecting electrical signals over a first time period, each of the electrical signals associated with at least one of the plurality of sensing electrodes, mixing the electrical signals to generate a biopotential dataset that includes permutations of the electrical signals, and identifying a target biopotential signal included in the one or more biopotential signals based, at least in part, on the biopotential dataset.

23 Claims, 7 Drawing Sheets

(51) Int. Cl.

| | | |
|---|---|---|
| A61B 5/256 | (2021.01) | |
| A61B 5/271 | (2021.01) | |
| A61B 5/28 | (2021.01) | |
| A61B 5/339 | (2021.01) | |
| A61B 5/352 | (2021.01) | |
| A61B 5/353 | (2021.01) | |
| A61B 5/355 | (2021.01) | |

(52) U.S. Cl.
CPC .............. *A61B 5/339* (2021.01); *A61B 5/352* (2021.01); *A61B 5/353* (2021.01); *A61B 5/355* (2021.01); *A61B 5/7203* (2013.01); *A61B 2562/043* (2013.01)

(56) References Cited

U.S. PATENT DOCUMENTS

| | | | |
|---|---|---|---|
| 9,526,433 | B2 | 12/2016 | Apetina et al. |
| 9,572,499 | B2 | 2/2017 | Gopalakrishnan et al. |
| 9,706,922 | B2 | 7/2017 | Cao |
| 10,052,042 | B2 * | 8/2018 | Jain .................. A61B 5/282 |
| 10,159,415 | B2 | 12/2018 | Gopalakrishnan et al. |
| 10,368,765 | B2 | 8/2019 | Huang et al. |
| 10,463,302 | B1 | 11/2019 | Ahmad et al. |
| 2005/0113703 | A1 * | 5/2005 | Farringdon ............ A61B 5/021 |
| | | | 600/509 |
| 2008/0269813 | A1 * | 10/2008 | Greenhut ............ A61N 1/0504 |
| | | | 607/36 |
| 2013/0281815 | A1 | 10/2013 | Varadan |
| 2016/0095527 | A1 * | 4/2016 | Thng .................. A61B 5/339 |
| | | | 600/382 |
| 2017/0354372 | A1 | 12/2017 | Varadan et al. |
| 2019/0099103 | A1 | 4/2019 | Lv et al. |
| 2019/0159676 | A1 | 5/2019 | Murphy et al. |
| 2020/0000355 | A1 | 1/2020 | Khair |

OTHER PUBLICATIONS

Rachim et al., Wearable Noncontact Armband for Mobile ECG Monitoring System, IEEE Transactions on Biomedical Circuits and Systems, 2016.

Abbaspour et al., Removing ECG Artifact from the Surface EMG Signal Using Adaptive Subtraction Technique, J Biomed Phys Eng 2014.

Elgendi et al., Revisiting QRS Detection Methodologies for Portable, Wearable, Battery-Operated, and Wireless ECG Systems, Plos One, Jan. 2014, vol. 9, Issue 1.

Escalona et al., Data-Driven ECG Denoising Techniques for Characterising Bipolar Lead Sets along the Left Arm in Wearable Long-Term Heart Rhythm Monitoring, www.mdpi.com/journal/electronics, 2017.

Kher, Signal Processing Techniques for Removing Noise from ECG Signals, Journal of Biomedical Engineering and Research.

Liu et al., A Cuffless Blood Pressure Measurement Based on the Impedance Plethysmography Technique, www.mdpi.com/journal/sensors, 2017.

Lynn et al., Arm and wrist surface potential mapping for wearable ECG rhythm recording devices: a pilot clinical study, J. Phys .: Conf. Ser. 450 012026, 2013.

Niswan et al., Wearable Non Contact Armband for Mobile ECG Monitoring System, International Journal of Innovative Research in Electrical, Electronics, Instrumentation and Control Engineering, vol. 6, Issue 2, Feb. 2018.

Yousefian et al., The Potential of Wearable Limb Ballistocardiogram in Blood Pressure Monitoring via Pulse Transit Time, www.nature.com/scientificreports, Jul. 23, 2019.

* cited by examiner

MULTI-LEAD MEASUREMENT OF BIOPOTENTIALS WITH WEARABLE DEVICE

CROSS-REFERENCE TO RELATED APPLICATION

This application claims the benefit of U.S. Provisional Application No. 63/063,005, filed Aug. 7, 2020, which is hereby incorporated by reference in its entirety.

TECHNICAL FIELD

This disclosure relates generally to measurement of biopotentials, and in particular but not exclusively, relates to wearable devices capable of biopotential measurements.

BACKGROUND INFORMATION

Biopotentials are generated by physiological processes occurring within a body that are produced by electrochemical activity of various cells, included in the heart, brain, eyes, skeletal muscles, skin, or the like. Such electrical activity may be monitored for characterizing the corresponding physiology. For example, the cardiac function of the heart may be assessed by sensing the electrical activity of the heart in the form an electrocardiogram (ECG), which may be particularly important to monitor as approximately 1 in every 4 deaths within the United States is due to cardiovascular related diseases. However, monitoring biopotentials accurately and continuously remains a challenge. In a clinical environment, an ECG machine may be utilized to produce a high quality snapshot of the heart electrical activity by measuring a cross-cardiac area, but may be limited in terms of portability, monitoring duration, and accessibility.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, method, and apparatus for multi-lead measurement of biopotentials are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "collecting", "measuring", "mixing", "identifying", "analyzing", "determining", "searching", "generating", "comparing", "modifying", "receiving", "providing", "displaying", "reconstructing", "tracking", "filtering", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such as information storage, transmission, or display devices.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, embodiments of the present disclosure are not described with reference to any particular programming language. It will be appreciated that a variety of programming languages may be used to implement the teachings of the disclosure as described herein.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
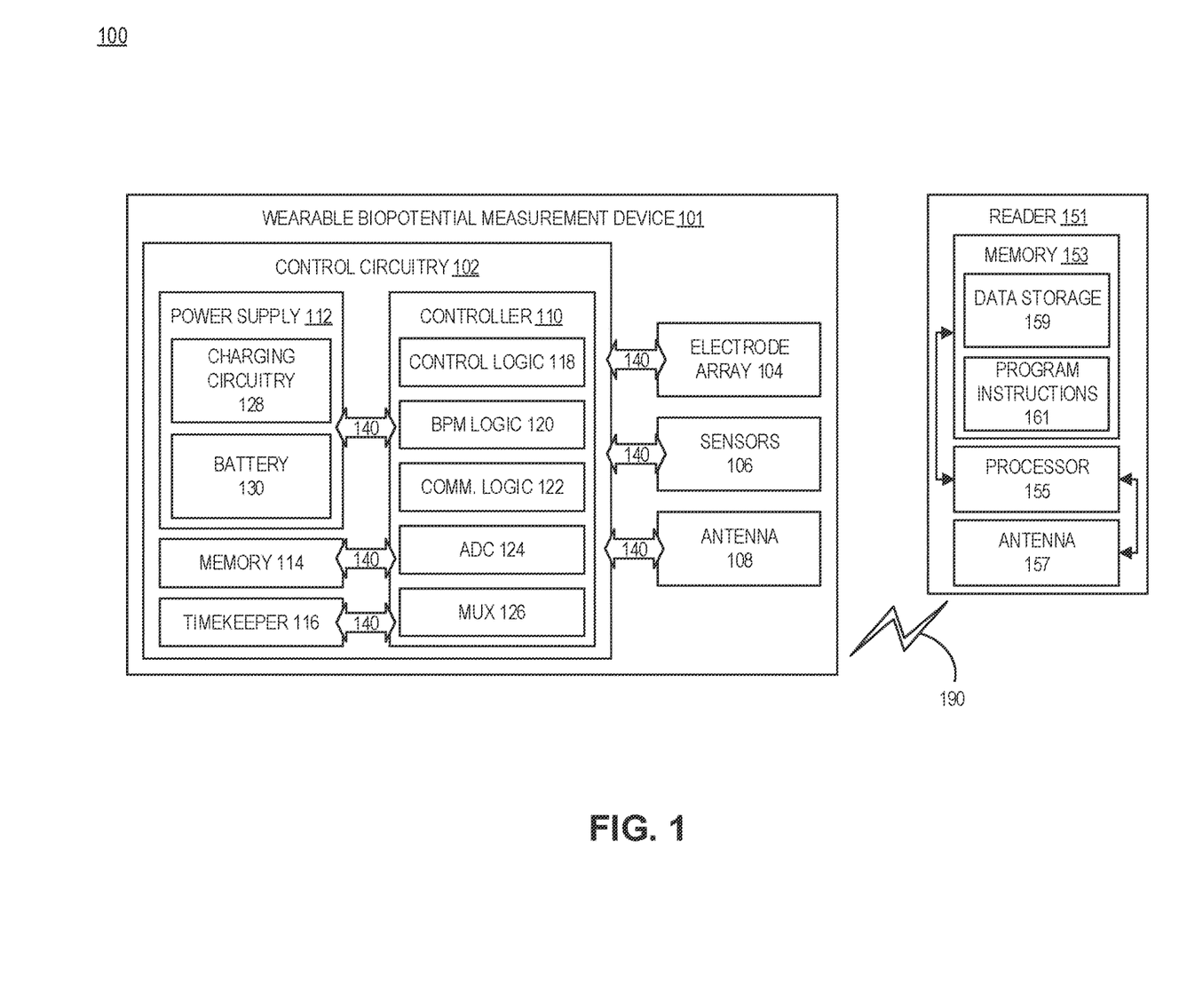
FIG. 1 illustrates a functional block diagram of a system including a wearable biopotential measurement device along with an external reader, in accordance with an embodiment of the disclosure.

FIG. 1 illustrates a functional block diagram of a system 100 including a wearable biopotential measurement device 101 along with an external reader 151, in accordance with an embodiment of the disclosure. In the depicted embodiment, wearable biopotential measurement device 101 includes control circuitry 102, electrode array 104, sensors 106, and antenna 108. The illustrated embodiment of control circuitry 102 includes controller 110, power supply 112, memory 114, and timekeeper 116. The illustrated embodiment of controller 110 includes control logic 118, biopotential measurement (BPM) logic 120, communication logic 122, analog-to-digital converter (ADC) 124, and multiplexer (MUX) 126. The illustrated embodiment of power supply 112 includes charging circuitry 128 and battery 130. Furthermore, as illustrated, the various components of the wearable biopotential measurement device 101 are communicatively (e.g., electrically) coupled to each other via one or more interconnects 140.

Wearable biopotential measurement device 101 may be a wearable device that is easily removable and capable of measuring one or more biopotential signals over an extended period of time. Specifically, device 100 may use combinational array measurements and signal mixing to track biopotentials in amplitude, location, and time via biopotential mapping in the body volume. The one or more biopotential signals may include, but are not limited to, electrocardiogram (ECG) signals, electromyogram (EMG) signals, electroencephalogram (EEG) signals, electrooculogram (EOG) signals, electrodermal activity (EDA) signals, and/or any combination thereof. Information of the body may be extracted from the measured biopotential signals and may include, but are not limited to, respiratory rate (RR), heart rate variability (HRV), sleep state, and/or any combination thereof. Embodiments described herein will be discussed in reference to the biopotential signal being measured as an ECG signal, but it should not be deemed limiting, and that other biopotential signals may be measured in lieu of or in addition to the measured ECG signal.

The electrode array 104 may include a plurality of sensing electrodes that extend, at least partially, around a cross-sectional volume (e.g., of an appendage of a wearer such as an arm, leg, or any other volume of a body) of a wearer of the wearable biopotential measurement device 101. In some embodiments, the electrode array 104 may be arranged in a linear array to extend around a cross-sectional volume. In other embodiments, the electrode array 104 may not be arranged as a linear array. In some embodiments, the arrangement of the electrode array 104 may cover multiple regions of a wearer. The plurality of sensing electrodes may be dry electrodes without adhesives that are easily removed (e.g., for multi-use) and allow for continuous measurement of the biopotential signals. In the case of an ECG signal, the wearable biopotential measurement device 101 is able to measure the electrical activity of the heart without the cross-sectional volume extending over a cardiac area. In other words, the heart of the wearer does not necessarily need to be located within the cross-sectional volume covered by the plurality of sensing electrodes to measure the ECG signal. In other embodiments, the plurality of sensing electrodes may be placed in other areas depending on the type of biopotential signal being measured. Electrode based sensors 106 may include other various sensor types to provide feedback information to controller 110. For example, but not limited to, an accelerometer or gyroscope may be included in sensors 106 to provide positional, rotational, direction, and/or acceleration information to track movement of the device 101 when worn by a user.

Controller 110 contains logic to choreograph operation of the components of the wearable biopotential measurement device 101. Control logic 118 controls general operation and may provide a logical user interface, power control functionality, manage control of various inputs and outputs generated by components of device 101, and the like. Control logic 118, for example, may manage ADC 124 and multiplexer 126. ADC 124 may receive measurement data (e.g., in the form of electrical signals) from electrode array 104 and sensors 106. ADC 124 may convert the received measurement data to a digital format and provide the same to control logic 118 and/or BPM logic 120. In some embodiments, ADC 124 may be coupled to electrode array 104 and sensors 106 via MUX 126, which controls the inflow of data to the ADC 124. In some embodiments, MUX 126 may be configured for measuring voltages of different electrode combinations included in the electrode array 104.

BPM logic 120 may receive measurements (e.g., electrical signals corresponding to periodic voltage measurements) from the electrode array 104 when the wearable biopotential measurement device 101 is worn (i.e., sensing electrodes of the electrode array 104 are in direct contact with the wearer). The measurements may be processed and formatted to generate a biopotential dataset or map that may be searched for characteristic waveforms of one or more biopotential signals. More specifically, the BPM logic 120 may include one or more classifiers that search for a best target signal (e.g., an electrocardiogram signal) and non-target signals (e.g., an electromyogram signal, which may be considered noise when the electrocardiogram signal is the target signal) based on the characteristic waveforms found in the biopotential dataset/map. Each of the searched signals may have characteristic features (i.e., waveforms) that may be identified and ranked in terms of signal quality with respect to location within the biopotential map/cross-sectional volume to reconstruct and track the biopotential signals (e.g., the target and non-target signals) dynamically over time. In other words, the target and non-target signals are tracked in real time, with the non-target signal utilized for noise filtering and other signal processing.

Communication logic 122 provides communication protocols for wireless communication with external reader 151 via antenna 108. Representative wireless communication protocols include, but are not limited to, Wi-Fi, Bluetooth, LTE, 5G, and the like. It is appreciated that controller 110 may not show all logic modules, all of which may be implemented in software/firmware executed on a general purpose microprocessor, in hardware (e.g., application specific integrated circuits), or a combination of both.

Power supply 112 supplies operating voltages to controller 100 and various other sensors and components of device 101 (e.g., electrode array 104, sensors 106, antenna 108, memory 114, and/or timekeeper 116) and includes charging circuitry 128 and battery 130 (e.g., alkaline, lithium ion, and the like) to power the various components wearable biopotential measurement device 101. Battery 130 may be charged directly (e.g., via an external power source) and/or inductively (e.g., via antenna 108 functioning as an energy harvesting antenna) with charging circuitry 128.

Charging circuitry 128 may include a rectifier/regulator to condition energy for charging battery 130 or directly powering controller 110 without battery 130 (e.g., when the wearable biopotential measurement device 101 is connected to an external power source). Charging circuitry 128 may also include one or more energy storage devices to mitigate high frequency variations when charging the battery 130 and/or directly powering the controller 110. For example, one or more energy storage devices (e.g., a capacitor, an inductor, and the like) can be connected to function as a low-pass filter.

Memory 114 is a non-transitory machine-readable storage medium that may include, without limitation, any volatile (e.g., RAM) or non-volatile (e.g., ROM) storage system readable by controller 110. Memory 144 may store information (e.g., measurement data in an unprocessed form, a processed form, or combination thereof), instructions (e.g., program instructions that when executed by the controller 110 cause the wearable biopotential measurement device 101 to perform operations or processes specified by the instructions), and the like.

Timekeeper 116 may be configured to provide a real time clock (RTC) for pairing measurement data with acquisition date and time. In some embodiments, measurement data is acquired at successive time steps over a period of time, which may be paired with information provided by the real time clock to generate a signal (e.g., voltage with respect to time). The timekeeper 116 may include a crystal oscillator operating at a frequency that provides sufficient time accuracy to measure one or more biopotential signals with the wearable biopotential measurement device 101. In some embodiments, controller 110 may include an internal oscillator (e.g., an RC oscillator) that may be used in place of timekeeper 116 or be calibrated by the oscillator of timekeeper 116.

It is noted that the block diagram shown in FIG. 1 is described in connection with functional modules for convenience in descriptions, but does not necessarily connote physical organization. Rather, embodiments of the wearable biopotential measurement device 100 may be arranged with one or more of the functional modules ("sub-systems") implemented in a single chip, multiple chips, in one or more integrated circuits, components, or otherwise.

It is appreciated that in the illustrated embodiment of FIG. 1, the wearable biopotential measurement device 101 is a self-contained or unified wearable device capable of measuring one or more biopotential signals over an extended period of time. For example, in one embodiment there may be housing that is coupled to control circuitry 102, electrode array 104, sensors 106, and antenna 108 such that the wearable biopotential measurement device 101 as a whole may be worn by the wearer. However, in other embodiments there may be non-wearable components of the wearable biopotential measurement device 101. In one embodiment the electrode array 104 may be wearable while the control circuitry 102 may be non-wearable or otherwise positioned at a separate location (e.g., handheld) than the electrode array 104. In the same or other embodiments, the electrode array 104 may be worn and configured or otherwise adapted to transmit (e.g., wirelessly or wired) the electrical signals to the control circuitry 102 for signal processing.

External reader 151 includes antenna 157 (or group of more than one antenna) to send and receive wireless signals 190 to and from wearable biopotential measurement device 101 via one or more communication protocols (e.g., Wi-Fi, Bluetooth, LTE, 5G, and the like). External reader 151 also includes a computing system with processor 155 in communication with memory 153. Memory 153 is a non-transitory computer-readable medium that can include, without limitation, a volatile (e.g., RAM) or non-volatile (e.g., ROM) storage system readable by the processor 155. Memory 153 can include a data storage 159 to store indications of data, such as data logs (e.g., user logs storing measurement data), program settings (e.g., adjust behavior of device 100 and/or external reader 151), etc. Memory 153 can also include program instructions 161 for execution by processor 155 to cause the external reader 151 to perform processes specified by the program instructions 161. For example, program instructions 161 can cause external reader 151 to provide a user interface that allows for retrieving information communicated from wearable biopotential measurement device 101 (e.g., measurement data) and/or allows for transmitting information to wearable biopotential measurement device 101. In some embodiments, the wearable biopotential measurement device 101 may provide feedback (e.g., haptic or otherwise) to a user (e.g., based on instructions from external reader 151).

External reader 151 can be a smart phone, digital assistant, or other portable computing device with wireless connectivity sufficient to provide the wireless communication link achieved with the wireless signals 190. In some embodiments, external reader 151 may be utilized by wearable biopotential measurement device 101 to offload one or more computational tasks (e.g., to preserve battery life). Thus, in some embodiments, the external reader 151 may receive measurement data, in real time or delayed, from wearable biopotential measurement device 101 and perform corresponding computational operations (see, e.g., method 700 of FIG. 7). In some embodiments the wearable biopotential measurement device 101 and/or external reader 151 may be coupled (e.g., wired, wirelessly, or otherwise) to external resources (e.g., cloud storage and/or computational resources) to store and/or analyze the measurement data.

Figure 2A:
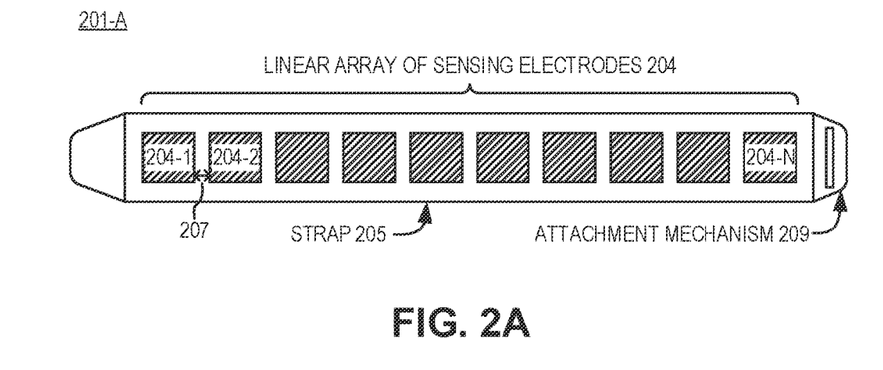
FIGS. 2A-2C illustrate various views of a wearable biopotential measurement device, in accordance with an embodiment of the disclosure.
Figure 2B:
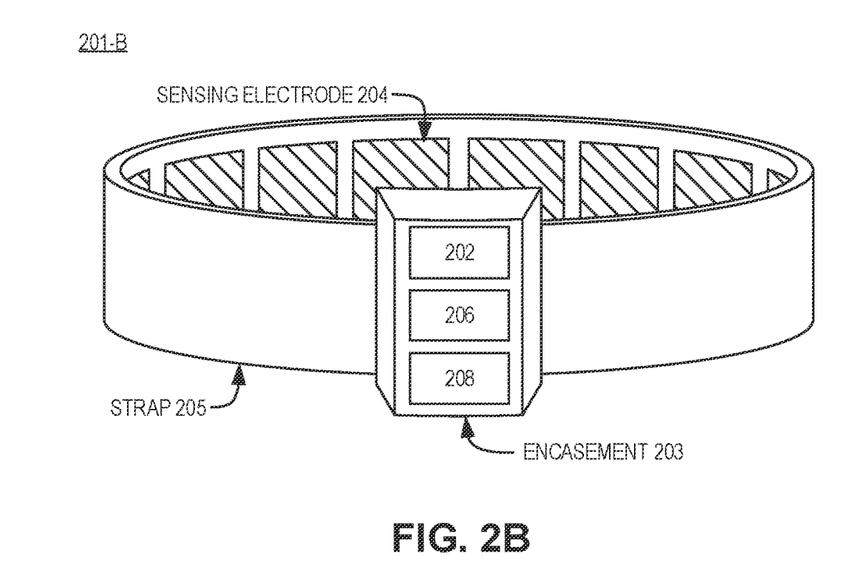
Figure 2C:
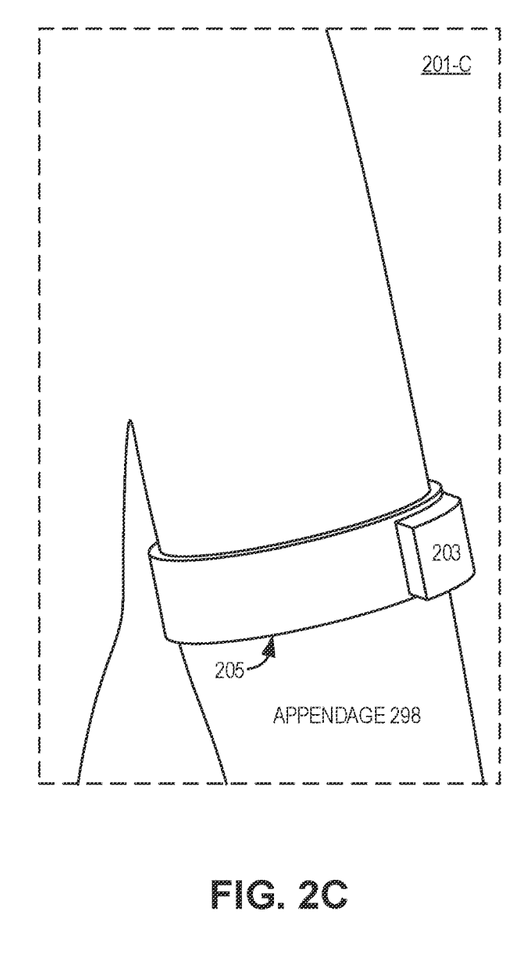

FIGS. 2A-2C illustrate various views of a wearable biopotential measurement device 201, in accordance with an embodiment of the disclosure. Wearable biopotential measurement device 201 is one possible implementation of device 101 illustrated in FIG. 1.

As illustrated, wearable biopotential measurement device 201 includes encasement 203, linear array of sensing electrodes 204, strap 205, and attachment mechanism 209. Encasement 203 may be a rigid housing that includes control circuitry 202, sensors 206, and antenna 206, which may be analogous to their like-named elements of wearable biopotential measurement device 101 illustrated in FIG. 1.

Each of the sensing electrodes has a definite length and width (e.g., extend over a pre-determined area) and are collectively arranged in a linear array on an inner surface of strap 205, such that when the wearable biopotential measurement device 201 is worn the linear array of sensing electrodes 204 extends, at least partially, around a cross-sectional volume of the wearer. In some embodiments, each of the sensing electrodes 204 included in the linear array is separated from a corresponding adjacent electrode (e.g., electrodes 204-1 and 204-2) by a common separation distance (e.g., 2.7 cm). In the same or other embodiments there may be N (e.g., 6, 7, 8, 10, or other integer quantity) sensing electrodes included in the linear array. It is appreciated that in the illustrated embodiment, the sensing electrodes 204 are arranged in a substantially linear manner. However, in other embodiments the sensing electrodes may be arranged differently (e.g., non-linearly) and/or with different separation distances between adjacent electrodes including in the sensing electrodes 204. Strap 205 is formed of a flexible material that includes two terminal ends that may be adhered to one another to form an adjustable length loop via attachment mechanism 209. Accordingly, wearable biopotential measurement device 201 may be attached to an appendage 298 (e.g., arm, leg, finger, or otherwise) of a wearer as shown in FIG. 2C. When worn, the plurality of sensing electrodes 204 may directly contact the wearer (e.g., skin of the wearer) for sensing one or more biopotential signals.

Figure 3:
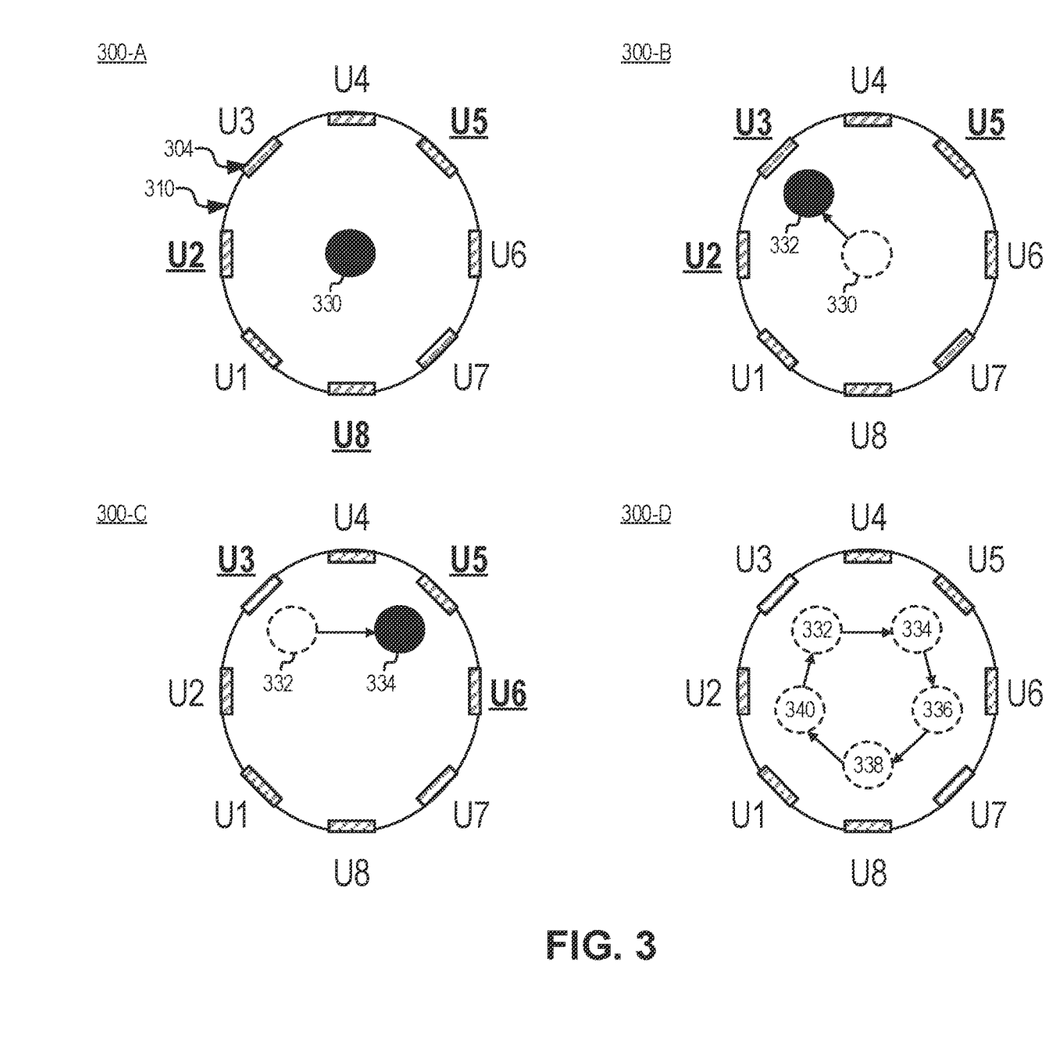
FIG. 3 illustrates measurement of different locations within a cross-sectional volume with example electrode combinations included in a wearable biopotential measurement device, in accordance with an embodiment of the disclosure.

FIG. 3 illustrates measurement of different virtual locations (e.g., 330, 332, 334, 336, 338, 340, or otherwise) within a cross-sectional volume 310 with example electrode combinations included in a wearable biopotential measurement device, in accordance with an embodiment of the disclosure. More specifically, FIG. 3 shows views 300-A through 300-D, in which different electrode combinations are activated to measure the electrical activity at different virtual locations within the cross-sectional volume 310 of the wearer of the device. It is appreciated that a measurement of a "virtual" location corresponds to an inferred electrical measurement of a location without an electrode disposed directly over or within said location. Thus, each of the views 300-A through 300-D show sensing electrodes 304 of a wearable biopotential measurement device individually labeled as U1-U8 (e.g., corresponding to the array of sensing electrodes 204 of FIGS. 2A-2C) and may be one possible implementation of device 101 illustrated in FIG. 1. Sensing electrical activity within the cross-sectional volume 310 may be obtained by measuring a potential difference (e.g., voltage) over time between different pairs or combinations of the electrodes 304. In the illustrated embodiment of FIG. 3, each of the electrodes may be paired with a common reference electrode (e.g., U1) and "activated," which is denoted by the bolded labels of views 300-A, 300-B, and 300-C. For example, when electrode U2 is "activated" as shown in view 300 of FIG. 3, a first electrical signal may be obtained by measuring the potential difference between electrode U2 and U1. Additional electrical signals may be obtained simultaneously for electrodes U3-U8, with each using electrode U1 as a reference electrode. In other embodiments, the reference electrode may not be included in the array of sensing electrodes or there may be no reference electrode.

In the illustrated embodiment of FIG. 3, the wearable biopotential measurement device extends around an upper arm of a wearer. Thus, when electrodes U2, U5, and U8 are activated, as shown in view 300-A, electrical activity of the center of the arm may be measured. When electrodes U2, U3, and U5 are activated, as shown in view 300-B, electrical activity proximate to the top left side of the arm may be measured. Similarly, when electrodes U3, U5, and U6 are activated, as shown in view 300-C, electrical activity proximate to the top right side of the arm may be measured. Thus, as shown in view 300-D various permutations of the sensing electrodes may be utilized to move the measurement location about the arm. Advantageously, each electrical signal obtained from the array of sensing electrodes 304 may be associated with a corresponding location and orientation within the arm. Quality of the electrical signal may differ depending on the location of the measurement within the cross-sectional area. Thus, the wearable biopotential measurement device may use the sensing electrodes to effectively "lock-in" the most useful signal even if the location of the signal changes over time. In some embodiments, multiple biopotential signals may be tracked (e.g., an ECG signal and an EMG signal which may be utilized to remove noise from the ECG signal) with the electrical signals obtained from the plurality of sensing electrodes.

In some embodiments, one or more of the signals obtained from each of the sensing electrodes may be processed to be representative of the potential difference at a given one of the electrodes (e.g., U2 through U8) with respect to a virtual reference location, such as a voltage center. For example, each electrical signal may be obtained by measuring the potential difference between two locations. In one embodiment, signals for each of the individual locations (e.g., 330, 332, 334, 336, 338, 340) are obtained by comparing the potential difference between a given sensing electrode (e.g., U2 through U8) to a reference electrode (e.g., U1). For example, a signal for the location proximate to the U2 electrode may correspond to the difference between electrodes U2 and U1 (e.g., V_U2−V_U1 or some other reference signal V_Ref) and so on. However, the calculated signal may change depending on a given reference signal or location (e.g., using a different electrode than U1). In some embodiments, the signals may be further processed such that the location of the reference signal is representative of a more meaningful location, which is advantageous for certain data analysis. For example, the center of the arm is a meaningful reference location, but may not be directly accessible.

However, the biopotential at a virtual location 330 corresponding to the center of the arm (e.g., when the plurality of sensing electrodes 304 extend around an arm when worn), or any other location (e.g., 332, 334, 336, 338, 340, or otherwise) that the wearable device extends around (e.g., corresponding to cross-sectional volume 310 which is defined by the placement of the plurality of sensing electrodes 304), can be obtained based on raw measurement data from the plurality of sensing electrodes 304. For example, an electrical signal associated with the virtual location 330 (e.g., a virtual center of the cross-sectional volume 310) with respect to a real reference location (e.g., U1) may be calculated as ((V_U2−V_Ref)+(V_U5−V_Ref)+(V_U8−V_Ref))/3, which is equal to (V_U2+V_U5+V_U8)/3−V_Ref. Then, in some embodiments, electrical signals associated with each of the plurality of sensing electrodes 304 (e.g., U2-U8) may be recalculated using the virtual center 330 as a virtual reference location, V_VRef based on a real reference location (e.g., U1). For example, the electrical signal associated with the location of sensing electrode U3 may correspond to V_U3−V_VRef, which can be calculated as (V_U3−V_Ref)−((V_U2+V_U5+V_U8)/3−V_Ref), which is V_U3−((V_U2+V_U5+V_U8)/3). It is appreciated that measurement of potential differences is relative measurement and thus we measure V_UX−V_Ref rather than the location of UX (e.g., U2 through U8) directly.

With the help of the virtual center concept described above, a biopotential measurement associated with a specific location within the cross-sectional volume defined by the plurality of sensing electrodes 304 is achievable as illustrated in FIG. 3. For example, for the view 300-B, a biopotential measurement of the virtual center may be calculated as (U2+U5+U8)/3, which corresponds to ((V_U2−V_Ref)+(V_U3−V_Ref)+(V_U5−V_Ref))/3−((V_U2+V_U5+V_U8)/3−V_Ref). Subtraction is a more straightforward process as V_Ref will be automatically removed during this process. For example, measurement of the location associated with the difference between U5−U3 corresponds to (V_U5−V_Ref)−(V_U3−V_Ref), which is equal to V_U5–V_U3. In some embodiments, this is the same as measuring the potential difference between U5 and U3 directly (V_U5–V_U3). In such a manner, electrical signals associated for each of the plurality of sensing electrodes 304 (e.g., U2-U8) may be collected (e.g., measured and stored in memory). Advantageously, direct access to the location is not necessary to obtain a target measurement of a given location (or relative difference between different locations) by using a virtual reference location.

Figure 4:
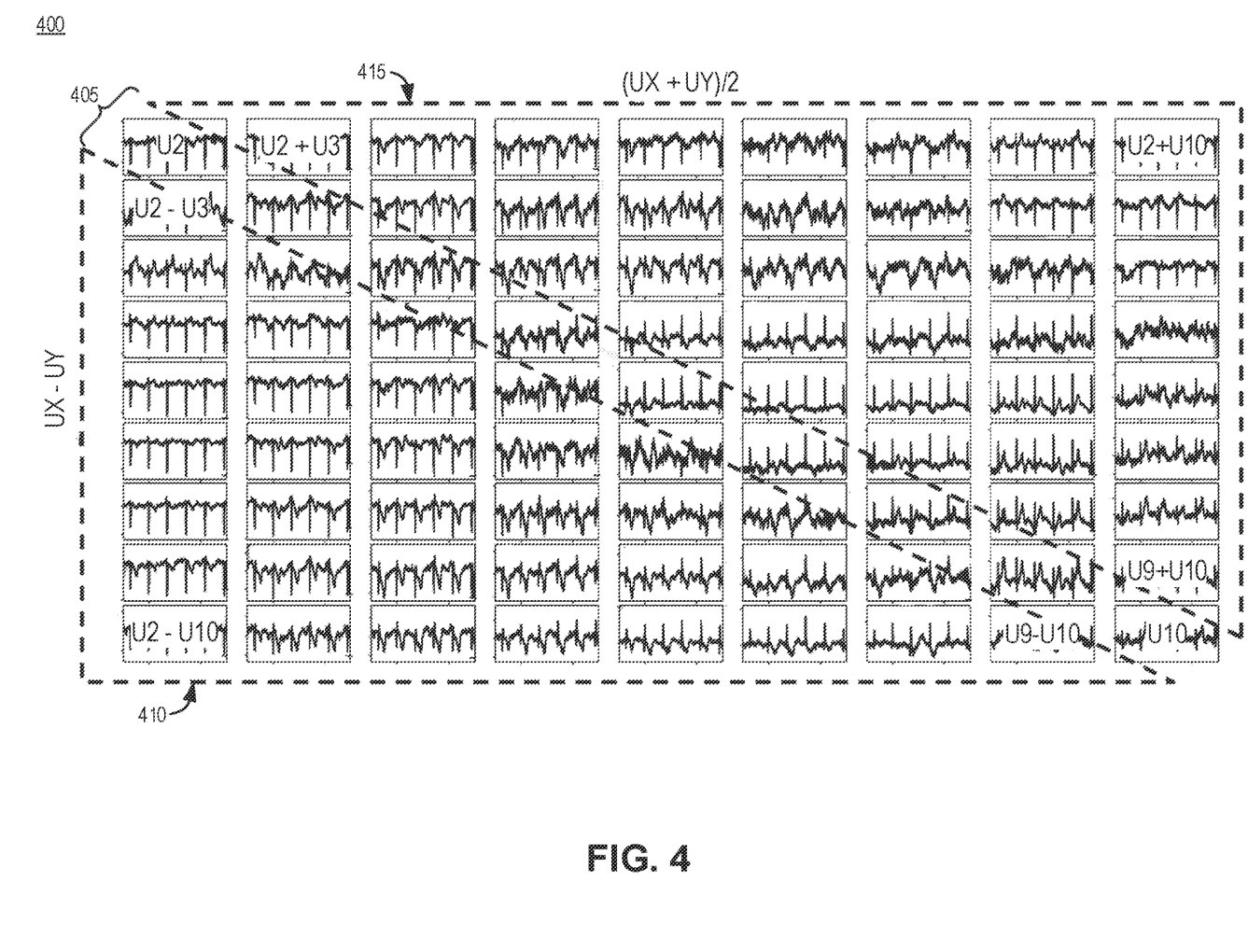
FIG. 4 illustrates an example biopotential dataset generated with a wearable biopotential measurement device, in accordance with an embodiment of the disclosure.

FIG. 4 illustrates an example biopotential dataset 400 generated with a wearable biopotential measurement device, in accordance with an embodiment of the disclosure. More specifically, biopotential dataset 400 may be generated by mixing (e.g., adding, subtracting, multiplying, dividing, or otherwise manipulating) one or more electrical signals obtained from a plurality of sensing electrodes (e.g., as shown in FIG. 3). Each of the electrical signals are associated with at least one of the plurality of sensing electrodes (e.g., U2-U10), which may be measured based on a real reference location, a virtual reference location, no reference location. An unprecedented level of data representative of electrical activity within a cross-sectional volume may be obtained. For example, nine electrodes mixed yield at least eighty-one unique measurements. It is noted that an additional electrode (e.g., U1 as illustrated in FIG. 3) is used as a reference for a total of ten electrodes. Each of the nine electrodes (e.g., U2-U10) are associated with a corresponding location within the cross-sectional volume (e.g., as described in FIG. 3). In some embodiments, the electrical signals may be processed (e.g., mixed) to generate signals representative of biopotential measurements mapped to a given location within the cross-sectional volume covered by the arrangement of the plurality of sensing electrodes (e.g., processed to be representative of a measurement with respect to the location of the sensing electrode relative to a center of the cross-sectional volume).

As illustrated in FIG. 4, different permutations of the electrical signals U2-U10 may be mixed to generate the biopotential dataset 400 for identifying one or more biopotential signals. Each element of the biopotential dataset 400 shows a voltage measurement with respect to time for various individual sensing electrodes or electrode combinations. Section 405 of the biopotential dataset 400 shows example electrical signals U2 (top left corner) through U10 (bottom right corner), each corresponding to a different location within a cross-sectional volume of a body being measured by a wearable biopotential measurement device. For example, the measurement labeled "U2" may correspond to the voltage measurement over a first period of time for U2 with respect to a real reference location (e.g., proximate to the location of the electrode U1 illustrated in FIG. 3) or a virtual reference location (e.g., location 330 illustrated in FIG. 3). Section 410 of the biopotential dataset 400 shows differencing between electrical signals (e.g., UX–UY), which may cover all permutations of the electrical signals in which two of the electrical signals may be subtracted from one another (e.g., U2-U3, U2-U10, U9-U10, and the like). Section 415 of the biopotential dataset 400 shows average of electrical signals (e.g., (UX+UY)/2), which may cover all permutations of the electrical signals in which pairs of electrical signals are averaged together. In various embodiments of the disclosure, each of the labeled reference measurements may be based on a real or virtual location. For example, in section 410, U2-U3 may be determined with respect to a real reference location (U1 illustrated in FIG. 3) or a virtual reference location (e.g., virtual location 330 illustrated in FIG. 3). Similarly, measurements included in section 415 may be based on a real or virtual reference location. It is appreciated that the described example of permutations should not be deemed limiting and that the quantity and method of mixing the electrical signals may vary in accordance to embodiments of the present disclosure.

Figure 5A:
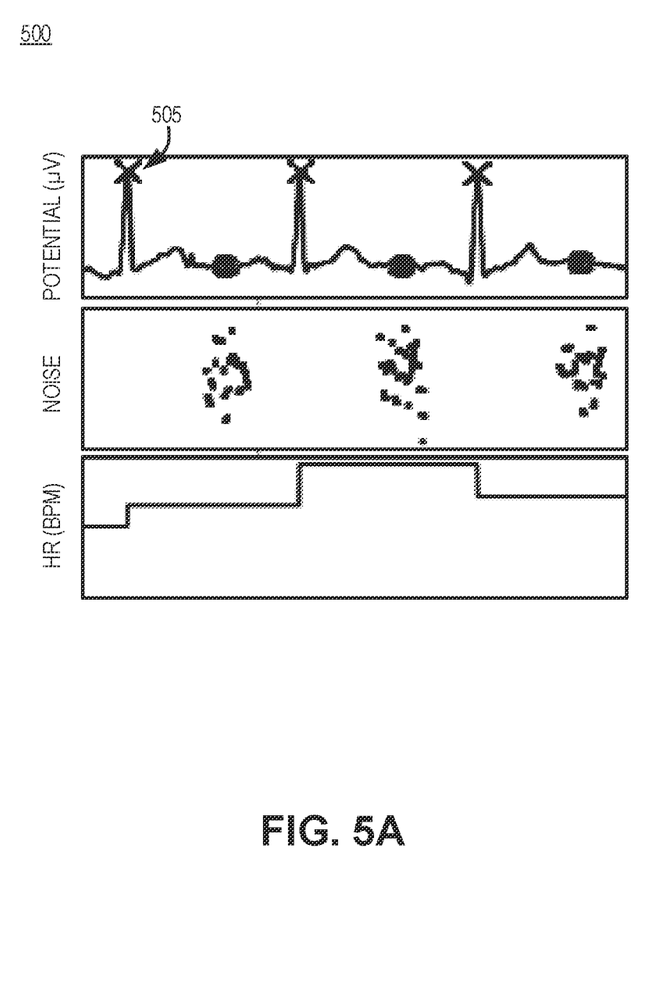
FIG. 5A illustrates an example classifier for searching a biopotential dataset to identify a characteristic waveform of a biopotential signal, in accordance with an embodiment of the disclosure.

FIG. 5A illustrates an example classifier 500 for searching a biopotential dataset to identify a characteristic waveform of a biopotential signal, in accordance with an embodiment of the disclosure. The classifier 500 may be an algorithm, set of instructions, or other characterization tool applied to each element of a biopotential dataset (e.g., biopotential dataset 400 shown in FIG. 4) to search for one or more characteristic waveforms of a biopotential signal. For example, if the biopotential signal is an ECG signal, the characteristic waveforms to be identified may be the R-wave, P-wave, T-wave, PR interval, QT interval, and the like. Classifier 500 is configured to search a selected element 505 (or combination of elements) of a biopotential dataset to search for the R-wave with respect to time (e.g., R-R interval monitoring), which may be utilized to determine heart rate of the wearer of the wearable biopotential measurement device, respiratory rate by evaluating the R-wave amplitude, shape, other metrics, or combinations thereof. In particular, the classifier 500 may identify a peak amplitude of the R wave for each interval as indicated by the "X" in the illustrated embodiment. The center panel of classifier 500 illustrates regional noise annotated by the circular markers in the top panel, which may be utilized for filtering and/or conditioning the signal being analyzed. In some embodiments, additional techniques for analysis of the biopotential dataset may include determining a moving average and/or baseline wandering of a given biopotential signal.

Figure 5B:
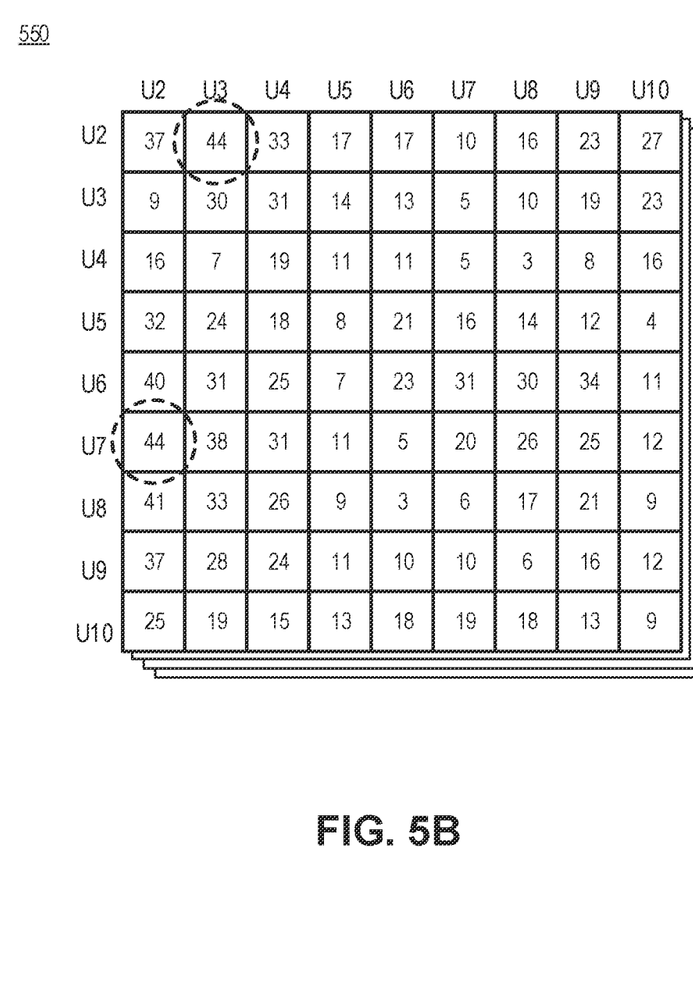
FIG. 5B illustrates an example feature map generated based on an identified characteristic waveform of a biopotential signal, in accordance with an embodiment of the disclosure.

FIG. 5B illustrates an example feature map 550 generated based on an identified characteristic waveform of a biopotential signal, in accordance with an embodiment of the disclosure. More specifically, the feature map relates location within a cross-sectional volume (e.g., based on the electrode permutations used to obtain an element of the feature map), amplitude, or other desired characteristic within the waveform. Thus, feature map 550 allows for dynamic tracking of characteristic waveforms (and thus the corresponding biopotential signal) based on, but not limited to, strength, location, and time. In the illustrated embodiment, for example, each element of feature map 550 has a value associated with a magnitude of a R-wave peak at a particular point (or range) of time. Each layer of the feature map 550 corresponds to a given time period. Amplitude peaks, or other features in the complex, may be identified and indicate the location of the strongest signal or signals for a given characteristic waveform (e.g., U2-U3 and U7-U2 as shown) at a given time. The amplitude peaks may be tracked over time and may be utilized to generate an adjusted characteristic waveform that combines (e.g., based on location) the strongest signals of the feature map 550 together. In some embodiments, the location of the strongest signal of the feature map 550 may change with respect to time (e.g., amplitude peak location for each layer may change). Thus, in one or more embodiments, the strongest signals may also be temporally combined (e.g. to produce an adjusted characteristic waveform that extends over the time period covered by all layers of the feature map 550). Advantageously, the feature map 550 allows for dynamic tracking of one or more biopotential signals within a cross-sectional volume over a period of time even as the locations within the cross-sectional volume with the highest sensitivity to the one or more biopotential signals change over time.

Figure 6:
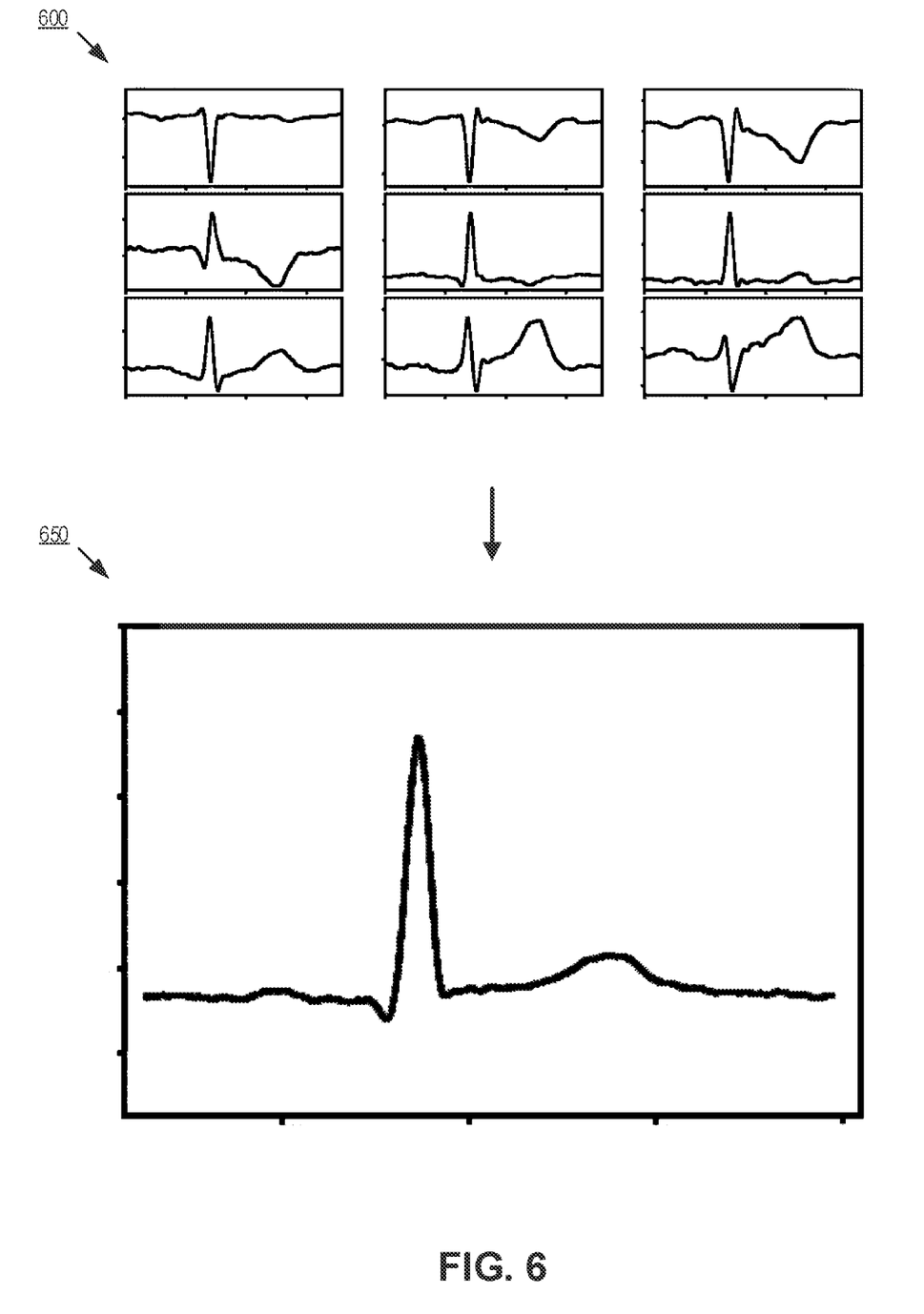
FIG. 6 illustrates a reconstructed biopotential signal generated based, at least in part, on one or more characteristic waveforms identified from a biopotential dataset, in accordance with an embodiment of the disclosure.

FIG. 6 illustrates a reconstructed biopotential signal 650 generated based, at least in part, on one or more characteristic waveforms 600 identified from a biopotential dataset, in accordance with an embodiment of the disclosure. More specifically, the adjusted characteristic waveforms (e.g., identified from one or more feature maps as shown in FIG. 5B) may be combined to reconstruct the biopotential signal. For example, ECG measurements from the array of sensing electrodes may be combined and the multi-lead ECG complex may be generated as a reconstructed biopotential signal.

Figure 7:
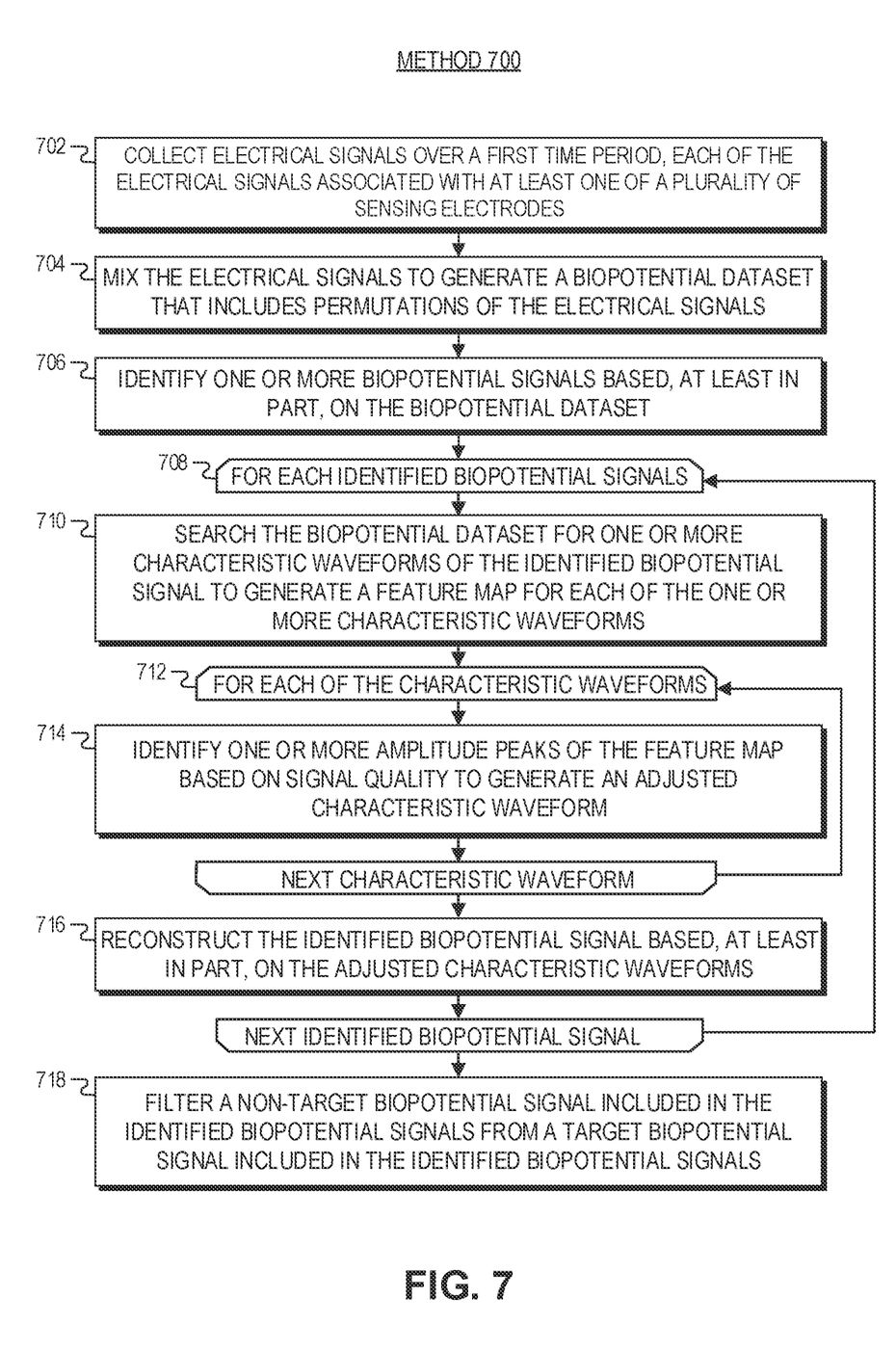
FIG. 7 illustrates a method for multi-lead measurement of biopotentials, in accordance with an embodiment of the disclosure.

FIG. 7 illustrates a method 700 for multi-lead measurement of biopotentials, in accordance with an embodiment of the disclosure. Method 700 may be implemented with the wearable biopotential measurement devices described herein (e.g., device 100 illustrated in FIG. 1 and device 200 illustrated in FIG. 2A-2C). It is appreciated that the order in which some or all of the process blocks appear in method 700 should not be deemed limiting. Rather, one of ordinary skill in the art having the benefit of the present disclosure will understand that some of the process blocks may be executed in a variety of order not illustrated, or even in parallel.

Block 702 shows collecting (e.g., measuring and storing in memory) electrical signals over a first time period, each of the electrical signals associated with at least one of a plurality of sensing electrodes. In some embodiments the electrodes of the plurality of sensing electrodes may be arranged in a linear array that extends around a cross-sectional volume of a wearer of the biopotential measurement device such that each electrode is associated with a respective perimeter location of the cross-sectional volume. In the same embodiment, each of the electrical signals may be collected by periodically measuring (e.g., sampling) the potential difference (i.e., voltage) between electrodes included in the linear array and/or a common reference electrode that may be included in the linear array or elsewhere (e.g., as discussed in reference to FIG. 3). The collected electrical signals may then be modified to be representative of one or more locations within the cross-sectional volume or otherwise be adjusted to be representative of a real or virtual location, in accordance with embodiments of the disclosure.

Block 704 illustrates mixing the electrical signals to generate a biopotential dataset that includes permutations of the electrical signals. The biopotential dataset may include the electrical signals (or representations thereof) and/or permutations of the electrical signals. The permutations may include groups of one or more electrical signals that are added, subtracted, multiplied, divided, or otherwise combined. In some embodiments, the biopotential dataset may include every permutation of the electrical signals for a given operation or processing technique. For example, the biopotential dataset may include the average of every paired combination of the electrical signals. In some embodiments, the electrical signals mixed are modified electrical signals associated with one or more locations within the cross-sectional volume with respect to a real or virtual location, in accordance with embodiments of the disclosure.

Block 706 shows identifying one or more biopotential signals based, at least in part, on the biopotential dataset. The one or more biopotential signals may include, but is not limited to, electrocardiogram (ECG) signals, electromyogram (EMG) signals, electroencephalogram signals (EEG), electrooculogram (EOG) signals, electrodermal activity (EDA) signal, and the like. Identification of the one or more biopotential signals may be based on one or more elements of the biopotential dataset in which characteristic waveforms or features are determined. For example, characteristic features of an R-wave, P-wave, T-wave, PR interval, QT interval, and the like found in one or more elements of the biopotential dataset may identify an ECG signal included in the one or more biopotential signals.

Block 708 illustrates an outer loop that indicates all elements within the outer loop may be applied to each of the identified biopotential signals. This may enable dynamic tracking or more than one biopotential signal (e.g., for filtering purposes).

Block 710 shows searching the biopotential dataset for one or more characteristic waveforms of the identified biopotential signal to generate a feature map for each of the one or more characteristic waveforms. Each feature map relates signal quality (e.g., amplitude) with a given one of the one or more characteristic waveforms. The characteristic waveforms correspond to a feature, pattern, or otherwise identifiable element that may describe, at least in part, the identified biopotential signal. For example, if the identified biopotential signal is an ECG signal, characteristic features may include the R-wave, P-wave, T-wave, PR interval, QT interval, and the like, which may be identified for each element of the biopotential dataset via one or more classifiers.

Block 712 illustrates an inner loop that indicates all elements within the inner loop may be applied to each of the characteristic waveforms identified, which may allow for tracking a best signal for each of the characteristic waveforms based on the corresponding feature map.

Block 714 shows identifying one or more amplitude peaks of the feature map based on signal quality to generate an adjusted characteristic waveform over a time period. Specifically, each layer of the feature map may correspond to a given time interval and each element within a given layer may correspond to a specific location within a cross-sectional volume. The location where the signal is strongest for a given one of the characteristic waveforms may change over time. Thus, a strongest signal or signals (e.g., based on amplitude) for each layer of the feature map may be tracked and subsequently combined to generate an adjusted characteristic waveform.

Block 716 illustrates reconstructing the identified biopotential signal based, at least in part, on the adjusted characteristic waveforms. For example, if the biopotential signal is an ECG signal and the characteristic waveforms include the R-wave, P-wave, T-wave, PR interval, QT interval, then the multi-lead ECG signal may be reconstructed by combining the adjusted characteristic waveforms.

Block 718 shows filtering a non-target biopotential signal included in the identified biopotential signals from a target biopotential signal included in the identified biopotential signals. For example, if the target biopotential signal is an ECG signal and the non-target biopotential signal is an EMG signal, the ECG signal may be enhanced by filtering out (e.g., removing or subtracting) the EMG signal from the ECG signal.

The processes explained above are described in terms of computer software and hardware. The techniques described may constitute machine-executable instructions embodied within a tangible or non-transitory machine (e.g., computer) readable storage medium, that when executed by a machine (e.g., controller 107) will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A biopotential measurement device, comprising:
a plurality of sensing electrodes adapted to measure one or more biopotential signals, wherein electrodes included in the plurality of sensing electrodes are configured for extension, at least partially, around a cross-sectional volume of a wearer of the biopotential measurement device when the plurality of sensing electrodes is worn; and
a controller coupled to the plurality of sensing electrodes and memory storing instructions that when executed by the controller cause the biopotential measurement device to perform operations including:
collecting electrical signals over a first time period, each of the electrical signals associated with at least one of the plurality of sensing electrodes;
mixing the electrical signals to generate a biopotential dataset that includes permutations of the electrical signals; and
searching the biopotential dataset for a first characteristic waveform of a target biopotential signal included in the one or more biopotential signals to generate a first feature map indicative of signal quality of the first characteristic waveform over the first time period with respect to a location within the cross-sectional volume.

2. The biopotential measurement device of claim 1, wherein each of the electrodes included in the plurality of sensing electrodes are separated from a corresponding adjacent electrode included in the plurality of sensing electrodes by a common separation distance.

3. The biopotential measurement device of claim 1, wherein the electrodes included in the plurality of sensing electrodes are further configured as a linear array.

4. The biopotential measurement device of claim 1, wherein the electrical signals are mixed such that the biopotential dataset includes measurements mapped to different locations within the cross-sectional volume, and wherein the memory includes additional instructions that when executed by the controller causes the biopotential measurement device to perform further operations including:
outputting a reconstruction of the target biopotential signal over the first time period based, at least in part, on the first feature map.

5. The biopotential measurement device of claim 4, wherein the memory includes additional instructions that when executed by the controller causes the biopotential measurement device to perform further operations including:
identifying one or more amplitude peaks of the first feature map based on the signal quality to generate an adjusted first characteristic waveform over the first time period.

6. The biopotential measurement device of claim 5, wherein the reconstruction of the target biopotential signal is further based, at least in part, on the adjusted first characteristic waveform.

7. The biopotential measurement device of claim 4, wherein the target biopotential signal is an electrocardiogram signal, and wherein the first characteristic waveforms is one of a P-wave, an R-wave, or a T-wave.

8. The biopotential measurement device of claim 1, wherein the memory includes additional instructions that when executed by the controller causes the biopotential measurement device to perform further operations including:
identifying a non-target biopotential signal included in the one or more biopotential signals based, at least in part, on the biopotential dataset.

9. The biopotential measurement device of claim 8, wherein the memory includes additional instructions that when executed by the controller causes the biopotential measurement device to perform further operations including:
dynamically tracking, in real time, respective locations within the cross-sectional volume of the target biopotential signal and the non-target biopotential signal.

10. The biopotential measurement device of claim 9, wherein the memory includes additional instructions that when executed by the controller causes the biopotential measurement device to perform further operations including:
filtering the non-target biopotential signal from the target biopotential signal to generate a reconstruction of the target biopotential signal.

11. The biopotential measurement device of claim 8, wherein the target biopotential signal is an electrocardiogram signal and the non-target biopotential signal is an electromyogram signal.

12. The biopotential measurement device of claim 1, wherein a heart of the wearer is not disposed within the cross-sectional volume when the biopotential measurement device is worn, and wherein the target biopotential signal is an electrocardiogram signal.

13. The biopotential measurement device of claim 1, wherein the plurality of sensing electrodes are dry electrodes.

14. The biopotential measurement device of claim 1, wherein the memory includes additional instructions that when executed by the controller causes the biopotential measurement device to perform further operations including:
outputting a reconstruction of the target biopotential signal over the first time period based, at least in part, on the first feature map.

15. At least one non-transitory machine-accessible storage medium that provides instructions which, when executed by a machine, will cause the machine to perform operations comprising:

receiving measurement data representative of electrical signals, each of the electrical signals associated with at least one electrode included in a plurality of sensing electrodes adapted to measure one or more biopotential signals over a first time period within a cross-sectional volume of a wearer of the plurality of sensing electrodes;

generating a biopotential dataset with the measurement data by mixing the electrical signals, wherein the biopotential dataset includes permutations of the electrical signals; and searching the biopotential dataset for a first characteristic waveform of a target biopotential signal included in the one or more biopotential signals to generate a first feature map indicative of signal quality of the first characteristic waveform over the first time period with respect to a location within the cross-sectional volume.

16. The at least one non-transitory machine-accessible storage medium of claim 15, wherein the electrical signals are further representative of an output of a biopotential measurement device including the plurality of sensing electrodes, wherein electrodes included in the plurality of sensing electrodes are configured in an array for extension, at least partially, around the cross-sectional volume of the wearer of the plurality of sensing electrodes when the biopotential measurement device is worn.

17. The at least one non-transitory machine-accessible storage medium of claim 16, wherein the electrical signals are mixed such that the biopotential dataset includes measurements mapped to different locations within the cross-sectional volume, wherein the non-transitory machine-accessible storage medium provides additional instructions which, when executed by the machine, will cause the machine to perform further operations comprising:

outputting a reconstruction of the target biopotential signal over the first time period based, at least in part, on the first feature map.

18. The at least one non-transitory machine-accessible storage medium of claim 17, that provides additional instructions which, when executed by the machine, will cause the machine to perform further operations comprising:

identifying one or more amplitude peaks of the first feature map based on the signal quality to generate an adjusted first characteristic waveform over the first time period.

19. The at least one non-transitory machine-accessible storage medium of claim 18, wherein the reconstruction of the target biopotential signal is further based, at least in part, on the adjusted first characteristic waveform.

20. The at least one non-transitory machine-accessible storage medium of claim 17, wherein the target biopotential signal is an electrocardiogram signal, and wherein the first characteristic waveforms is one of a P-wave, an R-wave, or a T-wave.

21. The at least one non-transitory machine-accessible storage medium of claim 16, that provides additional instructions which, when executed by the machine, will cause the machine to perform further operations comprising:

identifying a non-target biopotential signal included in the one or more biopotential signals based, at least in part, on the biopotential dataset;

dynamically tracking, in real time, respective locations within the cross-sectional volume of the target biopotential signal and the non-target biopotential signal; and filtering the non-target biopotential signal from the target biopotential signal.

22. The at least one non-transitory machine-accessible storage medium of claim 21, wherein the target biopotential signal is an electrocardiogram signal and the non-target biopotential signal is an electromyogram signal.

23. At least one non-transitory machine-accessible storage medium that provides instructions which, when executed by a machine, will cause the machine to perform operations comprising:

receiving measurement data representative of electrical signals obtained by sensing biopotential signals with a biopotential measurement device, the biopotential measurement device including a plurality of sensing electrodes configured for extension, at least partially, around a cross-sectional volume of a wearer of the plurality of sensing electrodes when the biopotential measurement device is worn;

mixing the electrical signals to generate a biopotential dataset that includes permutations of the electrical signals;

identifying a target biopotential signal and a non-target biopotential signal based, at least in part, on the biopotential dataset, wherein the target biopotential signal and the non-target biopotential signal are each included in the biopotential signals;

dynamically tracking, in real time, respective locations within the cross-sectional volume of the target biopotential signal and the non-target biopotential signal; and filtering the non-target biopotential signal from the target biopotential signal.

* * * * *